United States Patent [19]

Georgiou et al.

[11] Patent Number: 5,316,940
[45] Date of Patent: May 31, 1994

[54] **CONSTITUTIVE SOLUBLE METHANE MONOOXYGENASE MUTANTS OF METHANOTROPHIC BACTERIA SUCH AS *METHYLOSINUS TRICHOSPORIUM* A.T.C.C. 55314**

[75] Inventors: George Georgiou, Austin; Patricia Phelps, Weir; Gerald E. Speitel, Jr., Austin, all of Tex.

[73] Assignee: Board of Regents, The University of Texas System, Austin, Tex.

[21] Appl. No.: 873,936

[22] Filed: Apr. 24, 1992

[51] Int. Cl.$^5$ ............... C12N 1/20; D06M 16/00; C02F 3/00

[52] U.S. Cl. ............... 435/252.1; 435/262; 435/262.5; 435/264; 435/261; 210/610; 210/611

[58] Field of Search ............... 435/252.1, 262.5, 264, 435/858; 210/610, 611

[56] References Cited

U.S. PATENT DOCUMENTS

| | | | |
|---|---|---|---|
| 4,269,940 | 5/1981 | Patel et al. | 435/148 |
| 4,587,216 | 5/1986 | Patel et al. | 435/123 |
| 4,954,258 | 9/1990 | Little | 210/611 |
| 5,013,665 | 5/1991 | Suzuki et al. | 435/244 |

OTHER PUBLICATIONS

Bedard, C. and Knowles, R. (1989) "Physiology, Biochemistry and Specific Inhibitors of $CH_4NH_4^+$ and CO Oxidation by Methanotrophs and Nitrifiers" *Microbiol. Reviews* 53(1):68–84.

Bowman, J. P., Sly, L. I., and Hayward, A. C. (1990) "Patterns of Tolerance to Heavy Metals Among Methane-Utilizing Bacteria", *Letters in Applied Microbiology*, 10:85–87.

Bradford, M. M. (1976) "A Rapid and Sensitive Method for the Quantitation of Microgram Quantities of Protein Utilizing the Principle of Protein-Dye Binding", *Anal. Biochem.* 72:248–252.

Brusseau, Gregory A., Tsien, Hsien-Chyang, Hanson, Richard S., and Wackett, Lawrence P. (1990) "Optimization of Trichloroethylene Oxidation by Methanotrophs and the Use of a Colorimetric Assay to Detect Soluble Methane Monooxygenase Activity", *Biodegradation*, 1:19–29.

Burrows, K. J., Cornish, A., Scott, D. and I. J. Higgins (1984) "Substrate Specificities of the Soluble and Particular Methane Monooxygenases of *Methylosinus trichosporium* OB3b", *J. Gen. Microbiol.*, 130:3327–3333.

Cardy, D. L. N., Laidler, V., Salmond, G. P. C., and Murrell, J. C. (1991) "Molecular Analysis of the Methane Monooxygenase (MMO) Gene Cluster of *Methylosinus trichosporium* OB3b". *Molecular Microbiology* 5(2):335–342.

Carlsen, H. N., Joergensen, L. and Degn, H. (1991) "Inhibition by Ammonia of Methane Utilization in *Methylococcus capsulatus* (Bath)" *Appl. Microbiol. Biotechnol.* 35:124–127.

Cornish, A., Nicholls, K. M., Scott, P., Hunter, B. K., Aston, W. J., Higgins, I. J., and J. K. M Sanders "In vivo $^{13}$C NMR Investigations of Methanol Oxidation by the Obligate Methanotroph *Methylosinus trichosporium* OB3b", *J. Gen. Microbiol.*, 130:2565–2575.

(List continued on next page.)

*Primary Examiner*—Douglas W. Robinson
*Assistant Examiner*—Deborah K. Ware
*Attorney, Agent, or Firm*—Arnold, White & Durkee

[57] ABSTRACT

Selection of mutant methanotrophic bacteria capable of efficiently degrading halogenated hydrocarbons typically found in numerous wastewater sources is described. The mutants are distinguishable from parental strains in having a unique resistance to the presence of copper while exhibiting unusually high degradation rates toward trichlorethylene. *Methylosinus trichosporium* A.T.C.C. 55314 strains are particularly good sources of the described mutants which may be obtained using a new method of selection and screening. The disclosed microorganisms may be immobilized on various matrices and are particularly adaptable for use in bioreactors. Further, the methanotrophic bacteria have antibiotic resistance to streptomycin or rifampicin B.

5 Claims, 10 Drawing Sheets

OTHER PUBLICATIONS

Dalton, H., Prior, S. D., Leak, D. J., and Stanley, S. H. (1984) "Regulation and Control of Methane Monooxygenase", In: *Microbial Growth of C1 Compounds*, R. L. Crawford and F. S. Hanson, editors.

Davis, K. I., Cornish, A. and Higgins, I. J. (1987) "Regulation of the Intracellular Location of Methane Mono-Oxygenase During Growth of *Methylosinus trichosporium* OB3b on methanol", *J. Gen. Microbiol.* 133:291–297.

De Flora, S., Zanacchi, P. Camoirano, A., Bennicelli, C. and Badolati, G. S. (1984) "Genotoxic Activity and Potency of 135 Compounds in the Ames Reversion Test and in a Bacterial DNA-Repair Test", *Mutation Res.* 133:161–198.

Ensley, B. D. (1991) "Biochemical Diversity of Trichloroethylene Metabolism", *Annu. Rev. Microbiol.*, 45:283–299.

Fan, A. M. (1988) "Trichloroethylene: Water Contamination and Health Risk Assessment," *Rev. Env. Contam. Toxicol*, 101:55–92.

Fliermans, C. B., Phelps, T. J., Ringelberg, D., Mikell, A. T., and D. C. White (1988) "Mineralization of Trichloroethylene by Heterotrophic Enrichment Cultures", *Appl. Env. Microbiol.*, 51(7):1709–1714.

Forstner, U., and G. T. W. Wittman (1979) *Metal Pollution in the Aquatic Environment*, Springer-Verlag. p. 356.

Green, T. (1983) "The Metabolic Activation of Dichloromethane and Chlorofluoromethane in a Bacterial Mutation Assay Using *Salmonella typhimurium*", *Mutation Res.*, 118:277–288.

Hall, Barry G. (1991) "Increased Rates of Advantageous Mutations in Response to Environmental Challenges", *ASM News*, 57(2):82–86.

Hansen, R. S., Tsien, H. C., Brusseau, G. A. and Wackett, L. P. (1990) "Biodegradation of Low-Molecular-Weight Halogenated Hydrocarbons by Methanotrophic Bacteria", *FEMS Microbiol. Lett.*, 87:273–278.

Henry, Susan M., and Grbic-Galic, Dunja (1990) "Effect of Mineral Media on Trichloroethylene Oxidation by Aquifer Methanotrophs", (1990) 20:151–169.

Infante, P. F. and Tsongas, T. A. (1987) "Mutagenic and Oncogenic Effects of Chloromethanes, Chloroethanes, and Halogenated Analogues of Vinyl Chloride," *Env. Sci. Res.*, 25:301–327.

Jongen, W. M. F., Alink, G. M., and Koeman, J. H. (1978) "Mutagenic Effect of Dichloromethane on *Salmonella typhimurium*", *Mutation Res.*, 56:245–248.

Laemmli, U. K. (1970) "Cleavage of Structural Proteins During the Assembly of the Head of the Bacteriophage T4", *Nature* (London) 277:680–685.

Little, C. Dane, Palumbo, Anthony V., Herbes, Stephen E., Lidstrom, Mary E., Tyndall, Richard L., and Gilmer, Penny J. (1988) "Trichloroethylene Biodegradation by a Methane-Oxidizing Bacterium", *Appl. Environ. Microbiol.*, 54(4):951–956.

McPheat, W. L., Mann, N. H., and H. Dalton (1987) "Isolation of Mutants of the Obligate Methanotroph *Methylomonas albus* Defective in Growth on Methane", *Arch. Microbiol.*, 148:40–43.

Nicolaidis, A. A., and A. W. Sargent (1987) "Isolation of Methane Monooxygenase-Deficient Mutants from *Methylosinus trichosporium* OB3b using Dichloromethane", *FEMS Microbiol. Lett.*, 41:47–52.

Oldenhuis, R., Vink, R. L. J. M., Jannsen, D. B., and Witholt, B. (1989) "Degradation of Chlorinated Aliphatic hydrocarbons by *Methylosinus trichosporium* OB3b Expressing Soluble Methane Monooxygenase", *Appl. Envir. Microbiol.*, 55(11):2819–2826.

Oldenhuis, R., Oedzes, J. Y., Van Der Waarde, J. J., and Janssen, D. B. (1991) "Kinetics of Chlorinated Hydrocarbon Degradation by *Methylosinus trichosporium* OB3b and Toxicity of Trichlorethylene", *Appl. Envir. Microbiol.*, 57(1):7–14.

Parsons, F., Wood, P. R. and DeMarco (1984) "Transformations of Tetrachloroethylene and Trichloroethylene in Microcosms and Groundwater", *J. Am. Water Works Assoc.*, 76:56–59.

Patel, R. N., Hou, C. T., Laskin, A. I., and Felix, A. (1982) "Microbial Oxidation of Hydrocarbons: Properties of a Soluble Methane Monooxygenase from a Facultative Methane-Utilizing Organism, *Methylobacterium* sp. Strain CRL-26", *Appl. Envir. Microbiol.*, 44(5):1130–1137.

Prior, Stephen D., and Dalton, Howard (1985) "The Effect of Copper Ions on Membrane Content and Methane Monooxygenase Activity in Methanol-Grown Cells of *Methylococcus capsulatus* (Bath)", *Journal of General Microbiology*, 131:155–163.

(List continued on next page.)

OTHER PUBLICATIONS

Rittmann, B. E. and McCarty, P. L. (1981) "Substrate Flux into Biofilms of Any Thickness", *J. Environ. Engrg. ASCE* 107: 831–849.

Stanley, S. H., Prior, S. D., Leak, D. J. and Dalton, H. (1983) "Copper Stress Underlies the Fundamental Change in Intracellular Location of Methane Mono-Oxygenase in Methane-Oxidizing Organisms: Studies in Batch and Continuous Cultures", *Biotechnol. Lett.*, 5(7):487–492.

Trevors, J. T., Mayfield, C. I., and Inniss, W. E. (1982) "Measurement of Electron Transport System (ETS) Activity in Soil," *Microbial Ecology* 8:163–168.

Tsien, H.-C. and Hanson, R. S. (1992) "Soluble Methane Monooxygenase Component B Gene Probe for Identification of Methanotrophs That Rapidly Degrade Trichloroethylene", *Appl. Env. Microbiol.* 58(3):953–960.

Tsien, H.-C., Brusseau, Gregory A., Hanson, Richard S., and Wackett, Lawrence P. (1989) "Biodegradation of Trichloroethylene by *Methylosinus trichosporium* OB3b", *Appl Env. Microbiol.* 55(12):3155–3161.

Wilson, J. T., and B. H. Wilson (1985) "Biotransformation of Trichloroethylene in Soil," *App. Env. Microbiol.* 49:242–243.

Dialog Search Report.

CONSTITUTIVE SOLUBLE METHANE MONOOXYGENASE MUTANTS OF METHANOTROPHIC BACTERIA SUCH AS *METHYLOSINUS TRICHOSPORIUM* A.T.C.C. 55314

BACKGROUND

1. Field of the Invention

The invention relates to soluble methane monooxygenase (sMMO) constitutive mutant strains of methanotrophic bacteria capable of degrading chlorinated hydrocarbons in the presence of copper. Also disclosed are methods of selecting methanotrophic bacteria to provide mutants deficient in particulate methane monooxidase (pMMO) activity with retained soluble MMO (sMMO) activity.

2. Description of Related Art

Chlorinated aliphatic solvents represent a major class of pollutants due to their widespread distribution in the environment and their toxic or carcinogenic effects. They are produced in large quantities and are the most frequently detected organic pollutants found in drinking water from groundwater sources (Fan, 1988). Trichloroethylene (TCE), a common contaminant, is a known carcinogen in animals and a suspected carcinogen in humans (Infante and Tsongas, 1987). It is also an especially recalcitrant compound in aquifers, and undergoes biodegradation only slowly (Parsons, et al., 1984).

Chloroform is another ubiquitous contaminant, particularly prevalent as a byproduct in water and wastewater treatment processes where chlorine is used as a disinfectant. Trace amounts may often be found in drinking water sources in areas close to commercial operations.

Methanotrophic bacteria are unusually active in degrading chlorinated hydrocarbons such as chloroform and trichloroethylene (TCE), (Wilson and Wilson, 1985). Methanotrophs are capable of growth with methane as their sole carbon and energy source. Although chloroform and TCE cannot serve as a sole carbon source, it is cometabolized by these organisms under aerobic conditions, removing as much as 99% of the TCE at concentrations as high as 50 mg/liter (Fliermans, et al., 1988).

Well over a hundred strains of methanotrophic bacteria have been isolated. Of these, *Methylosinus trichosporium* OB3b degrades TCE at a rate at least one order of magnitude faster than other pure or mixed cultures (Hansen, et al., 1990).

The key enzyme responsible for this high rate of TCE removal is a methane monooxygenase (MMO), the enzyme responsible for the first step in methane oxidation by these microbes. The bacterial methane monooxygenases have broad substrate specificity, and the specificity of the soluble form (sMMO) of the enzyme generally is broader than the particulate form (pMMO) found associated with stacked internal membranes. The sMMO form is less frequently found in methanotrophic bacteria, but has been reported in *Methylosinus trichosporium, Methylococcus capsulatus,* and *Methylobacterium sp.* strain CRL26 (Patel, et al., 1982). Following incubation with whole cells of *M. trichosporium* OB3b, or purified sMMO with added NADH reductant, TCE is more than 90% mineralized to $CO_2$ and $Cl^-$ (Oldenhuis, et al. 1989).

A major problem in the use of *M. trichosporium* in bioremediation projects lies in its expression of MMO. Of the two forms of this enzyme, pMMO is normally expressed, while sMMO is expressed only when cells are grown under copper limitation (Burrows, et al., 1989; Stanley, et al., 1983). Unfortunately, the levels of copper necessary to down-regulate the expression of sMMO are quite low, on the order of about 1 $\mu$M, which is within the range of copper ion levels found in groundwater (Forstner and Wittman, 1979).

Despite the knowledge that sMMO is required to metabolize TCE and related chlorinated hydrocarbons, there has been no success in developing or isolating a *M. trichosporium* capable of metabolizing TCE and related compounds in the presence of copper ion. Copper is ubiquitous in most water sources and particularly in polluted water; economically practical means of removal are not presently available.

SUMMARY OF THE INVENTION

The present invention addresses one or more of the foregoing problems in providing mutant strains of methanotrophic bacteria which have the ability to degrade chlorinated hydrocarbons under conditions that inhibit sMMO in wild-type methanotrophic bacteria. In particular, *M. trichosporium* mutants are especially useful for degrading certain chlorinated species in the presence of copper. The invention also relates to methods of isolating methanotrophic mutants. The mutants display a unique ability to degrade chlorinated hydrocarbons, e.g. trichloroethylene (TCE), in the presence of relatively high concentrations of copper. The disclosed mutants are stable, easily maintained in culture and have high sMMO activity.

Mutants of the present invention may be obtained from wild-type methanotrophic bacteria such as strain OB3b, recognized for an ability to efficiently metabolize halogenated substrates such as trichloroethylene (TCE). However, in contrast to the wild-type bacteria, the mutants of the present invention efficiently metabolize chlorinated substrates in the presence of copper ions. Efficient TCE metabolism has been observed in cultures of mutants grown at copper ion concentrations up to at least 15 $\mu$M. However, this is not necessarily a limiting level of copper ion as it may be expected that further improvements in the selection procedure will allow the isolation of mutants with even higher tolerances to copper ions.

Another aspect of the invention is an immobilized preparation of the disclosed mutants. Immobilization of wild-type *M. trichosporium* can lead to inhibition of sMMO expression because of the presence of bound copper on the immobilization matrix. This is not a problem with the disclosed mutants. OB3b mutants have been successfully immobilized on diatomaceous earth pellets. In this form, the mutants are effective in metabolizing TCE and other chlorinated hydrocarbons whereas wild-type cells show significantly less activity. Immobilization materials other than diatomaceous earth may also be employed, depending on the particular application. Examples of immobilization materials include sand, activated carbon, polyurethanes, glass beads, hydrophilic gels such as agar or carrageenans or plastic matrices. Immobilization may be by adsorption, entrapment or attachment to various materials by such means as covalent linking combined with glutaraldehyde cross-linking.

Immobilized preparations of *M. trichosporium* mutants are particularly suitable for use in various bioreactor systems. Flow through or batch type reactors might be used, although flow through reactors would be preferred. Flow rates into such systems could be adjusted depending on the contaminant levels in the flow stream. It is contemplated that maximum efficiency in the systems will be obtained by alternating cycles of microbial growth with pollutant degradation treatment. During the growth cycle, the microorganisms are contacted with a nutrient/air/methane mixture to allow growth and sMMO expression. During the degradation cycle, contaminated water is passed through the reactor for bioremediation.

Also contemplated as part of the invention are treatment processes for degrading halogenated hydrocarbons in aqueous solutions by contacting one or more of the disclosed mutants with the halogenated hydrocarbon. Such hydrocarbons might include trichloroethylene, as well as other trihalogenated, dihalogenated and monohalogenated short chain aliphatic hydrocarbons. Typical classes of compounds include generally the halogenated methanes, ethanes and ethenes and more particularly such species as dichloromethane, dibromomethane, chloroform, chloromethane, bromomethane, dichlorofluorethane and the like. Bioremediation conditions will vary depending upon the circumstances, the amount of material to be metabolized and the source of the contaminant. Sources of the contaminant will generally include groundwater, landfill leachate, storm water, drinking water, etc. Another source of halogenated hydrocarbon contaminants is gaseous effluents. Such gas streams may be equilibrated with an aqueous stream to allow transfer of the contaminant into the water stream. The water may then be subjected to bioremediation, as for example by the methods herein described.

Yet another aspect of the invention includes a method of isolating *M. trichosporium* OB3b mutants deficient in particulate MMO. The steps generally include culturing *M. trichosporium* OB3b and selecting mutants from the parent strain under selection conditions in which only mutants survive. Selected mutants, although lacking particulate MMO will exhibit sMMO activity. The selecting step is performed in the presence of dichloromethane (DCM, a suicide substrate, Nicolaidis and Sargent, 1987; McPheat, et al., 1987) and methanol. As used herein, a suicide substrate is a compound metabolized to a product or intermediate that is lethal to the organism. Dichloromethane, for example, is toxic to cells expressing MMO, possibly because carbon monoxide produced during metabolism and acts as a toxic agent (Nicolaidas and Sargent, 1987). Other compounds may work as well as DCM as a suicide substrate for pMMO. One requirement is that the substrate must be readily taken up but nontoxic to the cells unless it is oxidized by the pMMO enzyme. Generally, bacterial membranes are freely permeable to small hydrophobic molecules. Low molecular weight compounds oxidizable by pMMO, and therefore potentially suitable as suicide substrates, include chloroform, 1,2-dichloroethane, cis- and trans-1,2-dichloroethylene, 1,2-dichloropropane, 1,3-dichloropropane and the like. The suicide substrates need not be limited to chlorinated species as other halogenated compounds, including brominated species, or low molecular weight phosphorus compounds, might also be expected to exert similar effects on the cell. On the basis of the oxidation of propene to propene oxide by pMMO, there is also an expectation that 3-hydroxylpropene will be oxidized to 2,3-epoxy-1-propanol, a compound that is highly genotoxic (De Flora et al., 1984). Any of these compounds may also have a direct mutagenic effect on bacteria, leading to new species with altered genotype.

Addition of excess methanol with each dichloromethane addition appears to reduce the activation of DCM to toxic oxidation intermediates by colonies expressing sMMO. Furthermore, high levels of copper in the growth medium discourage the expression of sMMO. These two effects promote the isolation of mutants selectively deficient in the particulate forms of MMO. Survivors of the DCM/methanol/Cu selection procedure are isolated on methane-grown plates. This step selects for mutants that continue to express some form of the MMO enzyme.

An unusual aspect of practicing the disclosed methods of mutant isolation is the long culturing period. Culturing is continued for a relatively long period, generally at least two weeks, preferably three to five weeks, before transferring to liquid medium supplemented with copper ion. The mutants isolated under these conditions do not appear to be identical and it is contemplated that even longer periods of culture may select for mutants with improved or altered characteristics from those described. Preferred levels of copper ions for the selecting step are about 5 $\mu$M.

For the selection process, the microorganism may be grown on plates to determine the presence of sMMO. When plating on DCM plus methanol, the majority of the microorganisms will generally revert to wild-type phenotype. Plates employed for colony streaking are most preferably methane grown plates.

Yet another aspect of the invention is an assay for detecting MMO expression in bacterial colonies. Conventional means of determining sMMO expression is by analysis of naphthol formation in liquid culture. In the novel disclosed method, the naphthalene substrate is dissolved in a low-melting hydrogel matrix such as agarose, solidified over the surface of established bacterial colonies, incubated and then analyzed for the presence of naphthol produced by the oxidation of naphthalene by sMMO. The assay is quick and easy, permitting identification of individual colonies that produce the enzyme.

Although particularly advantageous for detection of sMMO on colonized plates, the method may also be employed to detect sMMO oxidation of naphthalene, or other suitable substrate, in liquid culture. Other substrates oxidizable by sMMO to form colorimetrically detectable products include compounds such as benzene, methoxy-p-nitrophenol and p-nitrobenzene. The overlay matrix is not limited to agar but may employ any of a number of hydrogel-like substances in which a substrate may be dispersed, so long as the matrix material does not interfere with sMMO expression. Preferably, the matrix will have the capacity to immobilize the oxidation product and the substrate at least to some degree while permitting enzyme access to the substrate. The addition of a surfactant, preferably Pluronic L-62, with a naphthalene substrate, provides improved results. While the exact function of surfactant is not clear, the use of other surfactants should not be precluded and it may be expected that other substrates will also benefit from the addition of surfactants. Numerous examples of surfactants are included in classes of nonionic, cationic and anionic species, such as Triton X-100, Tween 80, Pluronic F68 and the like.

DETAILED DESCRIPTION OF PREFERRED EMBODIMENTS

Figure 1:
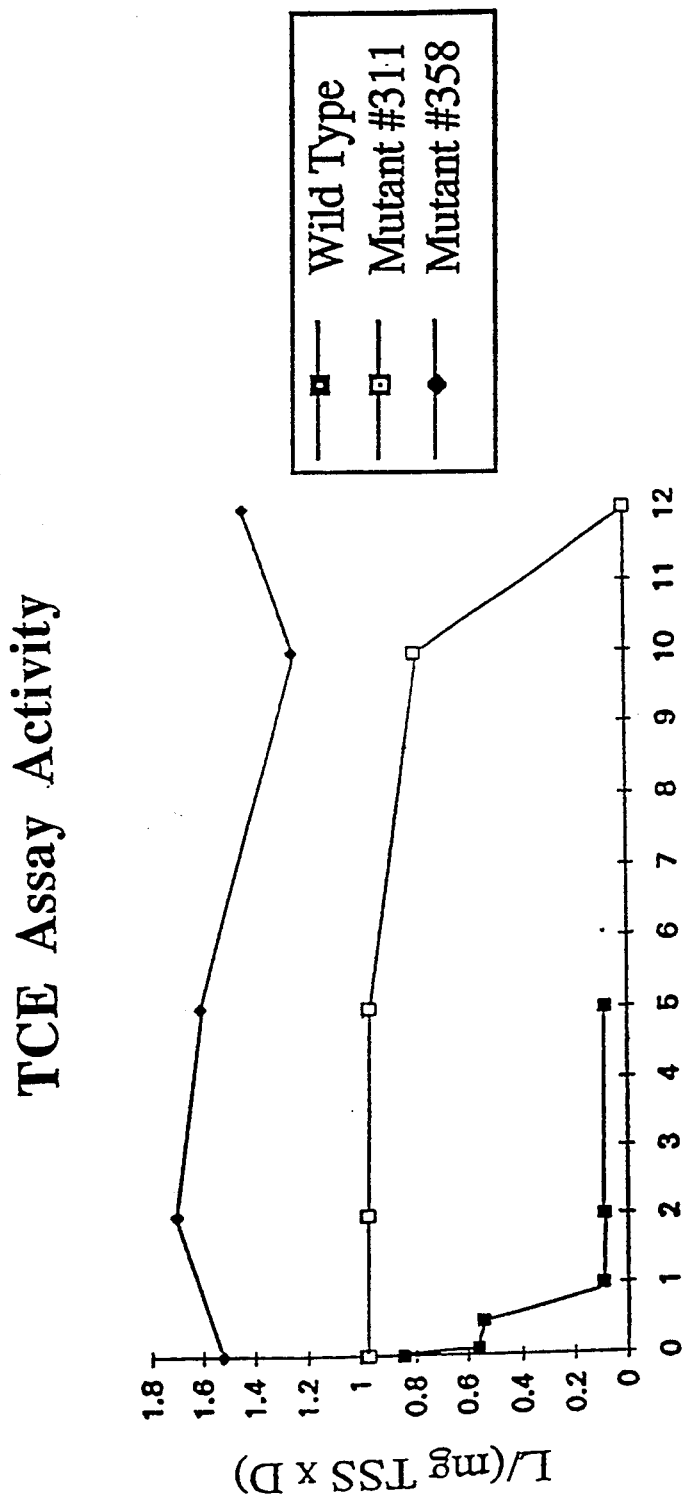
FIG. 1 shows effects of copper in growth medium on the expression of sMMO in wild-type and two methanotrophic mutants, PP311 and PP358. Enzyme activity of whole cells was assayed by TCE degradation at 1 mg/L TCE, reported as a pseudo first order rate constant (L/mg TSS/day).

The present invention provides a method of successfully isolating mutants of methanotrophic bacteria deficient in pMMO activity, while retaining expression of sMMO. These mutants are novel in being able to metabolize chlorinated hydrocarbons in the presence of copper, a serious limitation in wild-type M. trichosporium. MMO activity is not found in the particulate fraction in mutant cultures grown in 5 μM copper sulfate, a level at which wild-type cells express most of the MMO activity in the particulate fraction. The disclosed mutants, unlike the wild-type, efficiently degrade trichloroethylene in the presence of copper.

Many of the genes coding for sMMO enzyme components have been isolated (Cardy et al., 1991); however, recombinant technology has not successfully overcome the copper-sensitive problem in the wild-type M. trichosporium. This problem has been overcome with the mutants isolated and described herein.

DCM is a substrate for both the pMMO and sMMO enzyme, yielding oxidation products toxic to the organism expressing these activities. Plating on DCM and methanol medium selects for survivors deficient in MMO activity. Incorporation of 5 μM copper suppresses expression of sMMO. Maintaining high levels of methanol during selection also suppresses sMMO activity by competitive competition. In the present invention, an excess of methanol was periodically added with DCM addition and copper-containing (5 μM) medium to produce a large number of mutants that selectively lost ability to express pMMO. The number of such mutants obtained was about 30% of the DCM-resistant mutants.

The majority of the copper-resistant sMMO mutants grew poorly and were genetically unstable when subcultured on medium containing copper. Instability was evidenced by a high rate of reversion to the copper-sensitive phenotype. From the less than 25% of pMMO mutants that appeared stable, two new classes of mutants were obtained. One class (PP311 and PP319) grew slowly at >10 μM copper and expressed low levels of sMMO at higher concentrations. The other class (PP323, PP333 and PP358) adapted to wild-type growth rates in 12 μM copper and expressed high levels of sMMO at all levels of copper. These mutants were also stable and maintained the copper-resistant phenotype for at least 11 months of continuous subculturing. The stable copper-resistant mutants did not express pMMO and thus no MMO activity was found in the particulate fraction of cultures grown in 5 μM copper. This contrasted with wild-type cultures that expressed most of the MMO activity in the particulate fraction.

The procedure for selecting the disclosed mutant M. trichosporium encourages survival of sMMO+ colonies on DCM+methanol selection plates. These results are different from standard selections on DCM+methanol plates which typically produce mutants lacking both sMMO and pMMO activity. A high level of copper in the growth medium was used in the method of the present invention to promote expression of pMMO in plated cells, and addition of an excess of methanol with each DCM addition to further inhibit any sMMO activity contributed to the unexpected success in isolating the disclosed mutants.

The methanotrophic mutants of the present invention are especially suitable for use in bioreactor systems. When immobilized on a matrix such as diatomaceous earth pellets, mutants of M. trichosporium efficiently degrade chlorinated hydrocarbons such as TCE. By comparison, wild-type methanotrophs such as M. trichosporium OB3b degraded chlorinated hydrocarbons under the same conditions at much lower rates, presumably because of poisoning by residual copper concentrations in the diatomaceous earth matrix.

The mutant methanotrophs are expected to be well-adapted for use in a variety of bioreactors. These systems may be employed for degradation of contaminated water or for degradation of chlorinated hydrocarbon contaminants in gas streams. For example, a gas stream may be passed through an immobilized preparation of mutant M. trichosporium with a confluent water stream. The gas equilibrates with the water, facilitating dissolution of contaminants into the aqueous phase. Contact with the immobilized bacteria then initiates degradation of any chlorinated hydrocarbons in the aqueous medium.

At low concentrations of chlorinated solvents, degradation follows pseudo first order kinetics, described by:

$$r = -k_1 XS$$

where r is the degradation rate (mg/L/day), $k_1$ is the pseudo first order degradation rate constant (L/mg TSS/day), X is the cell concentration (mg TSS/l) and S is the chlorinated solvent concentration (mg/L). Pseudo first order rate constants may be estimated in suspended growth batch systems by direct application of the rate expression to the concentration versus time data. In attached growth, packed bed reactors, a biofilm computer model may be used in conjunction with the removal data and biomass measurements to indirectly estimate the rate constant. The magnitude of the rate constant is one basis for judging progress in the development of this technology.

MATERIALS AND METHODS

Cultures. *Methylosinus trichosporium* OB3b was obtained from the American Type Culture Collection (ATCC #35070) and cultured in Higgins minimal nitrate salts (HMNS) medium supplemented with 2 micromolar EDTA and copper sulfate at the indicated levels. Plates were made of the same medium, supplemented with 1.8% Noble agar (Difco), a purified grade of agar. Noble agar supported less fungal contaminant growth compared with less pure grades of agar. Plates were also prepared with 0.1 mg/ml cycloheximide to reduce problems with fungal contamination. Cross contamination of *M. trichosporium* OB3b with other methanotrophs was avoided by supplementing media with 0.05 mg/ml nalidixic acid.

Stock cultures were maintained by subculturing on plates every 3 weeks incubated in desiccators at room temperature with an atmosphere of approximately 50% methane.

Liquid cultures were prepared in sealed bottles or vials, with the liquid phase not exceeding 10% of the total volume. Liquid cultures were subcultured with a 4% (v/v) inoculum. Methane and oxygen was maintained in the headspace at 25% (v/v) each by daily supplementation.

Since methanotrophs are incapable of growth in rich medium, culture contamination by heterotrophic and facultative methanotrophic microbes was detected by colony formation on Plate Count Agar (Difco).

Culture Density. Absorbance of a cell suspension at 600 nm was used to estimate biomass. A conversion factor of 400 mg/L of total suspended solids (TSS) per absorbance unit was used.

Protein Determination. Protein was assayed by the Bradford method (Bradford, 1976) using bovine serum albumin as the reference standard. Proteins were determined spectrophotometrically at 595 nm after binding to Coomassie Brilliant Blue G-250.

Mutant *Methylosinus trichosporium* PP358

A mutant *M. trichosporium* deficient in pMMO isolated as herein described has been deposited with the American Type Culture Collection, 12301 Parklawn Drive, Rockville, Md. 20852 USA. Deposit was accepted for deposit Apr. 2, 1992 under the Budapest Treaty on the International Recognition of the Deposit Microorganisms for the Purposes of Patent Procedure. All restrictions on the availability to the public of the material so deposited will be irrevocably removed upon the granting of a patent. Mutant *M. trichosporium* PP358 has been accorded accession number ATCC 55314.

The examples which follow are intended to illustrate the practice of the present invention and are not intended to be limiting. Although the invention is demonstrated with selection of particular mutants, the same general selection methods will be applicable to other strains of methanotropic bacteria which grow on methanol and express sMMO. It should be possible to identify the loci responsible for lack of sensitivity to copper and then construct recombinant strains that exhibit copper resistance. It is understood that the invention disclosed herein is not necessarily confined to the particular elements illustrated and therefore may be practiced in the absence of any element not specifically disclosed or in the presence of additional elements.

EXAMPLE 1

The following example illustrates the selection procedure employed to isolate *M. trichosporium* mutants deficient in pMMO. In general principle, the method is based on the lethality of dichloromethane (DCM) toward cells expressing MMO. Metabolism of DCM yields carbon monoxide which is toxic to the cells. DCM is also known to be mutagenic in certain other types of cells. The method is designed to select mutants deficient in pMMO by plating in the presence of copper ions.

Selection of *M. trichosporium* Mutants Lacking MMO

Mutagenesis and Isolation of Mutants. Cultures grown in HMNS and 0.5% methanol as sole carbon source were plated on HMNS medium supplemented with 0.025% yeast extract, 5 micromolar copper sulfate, and 1% methanol. Yeast extract improved plating efficiency and promoted growth of colonies growing on methanol. Addition of 5 μM copper prevented expression of sMMO. Plates were incubated in an 11-liter desiccator to which 0.6 ml dichloromethane and 1.0 ml methanol was delivered every three days. Controls were incubated in desiccators supplemented with methanol alone.

Survival on dichloromethane and methanol was low. There were approximately 1 in $10^5$ colony forming units (CFU) compared with the methanol controls. Of 65 surviving colonies, approximately one-third failed to grow on plates incubated with methane (Table 1). However, the majority of the mutants retained ability to grow in methane as the sole carbon source.

TABLE 1

| Classification of DCM-resistant mutants | | |
|---|---|---|
| Classification | Total Number | % of Total |
| pMMO−, sMMO− | 21 | 32 |
| pMMO+, sMMO+ | 25 | 38 |
| pMMO−, sMMO+ | 19 | 29 |

Following 5 weeks of growth in the presence of dichloromethane, colonies were streaked onto HMNS plates, 50 streaks per plate. To assess the expression of MMO, duplicate plates were grown in the presence of methanol or methane. Colonies that grew on methane were transferred to HNMS plates supplemented with 5 μM copper. Initially, many of the MMO+ mutants failed to grow on the copper supplemented medium. Mutants were further classified by evaluating the expression of sMMO in the presence of copper. An in situ plate assay for naphthalene oxidation by sMMO in these mutants showed that nearly half of the surviving colonies expressed active sMMO in HMNS medium even when copper was present at 5 µM, FIG. 1, indicating they were defective in pMMO but not sMMO expression. A large proportion of DCM-resistant MMO+ mutants expressed pMMO in copper-containing medium and sMMO in copper-deficient medium, indicating wild-type phenotype.

After subculturing three times on methane-grown plates, 44 colonies were transferred to liquid HMNS medium supplemented with and without 2 micromolar copper sulfate. Expression of sMMO in the presence of copper was assessed using an in situ plate assay and by enzyme assay in liquid cultures. Many mutants had difficulty in adapting to growth in the liquid culture, having lag times as long as three weeks. Generally, mutants with the longest lag times had sMMO expression in the presence of copper. Of the 44 DCM mutants that retained ability to grow in methane, 19 expressed sMMO activity when grown in liquid culture, as determined by ability to oxidize naphthalene (Table 2) using the assay according to Example 6. Expression of sMMO in the presence of copper was assessed both on plate-grown colonies and in liquid cultures.

Activities were compared between cells grown without and cells grown in 2 micromolar copper ion. Table 1 shows that many of the mutants had high sMMO activity in the absence of copper while only one of the mutants, PP358, had comparable sMMO activity both with and without copper.

Most of the mutants grew slowly in the presence of 2 µM copper or were unstable, losing the copper-resistant sMMO phenotype and acquiring pMMO activity only after repeated subculturing. Of the original 19 sMMO mutants, 5 mutants (PP311, PP319, PP323, PP333 and PP358) grew well and continued to express sMMO in the presence of copper-containing medium with continuous subculturing. Three of the mutants (PP323, PP333 and PP358) continued to express sMMO even after nine months. Culture PP319 reverted to pMMO expression after 5 months and PP311 reverted after 7 months.

TABLE 2

Mutants retaining sMMO activity when grown in the presence of 2 µM Cu. sMMO Activity[1]

|  | grown without Cu | grown with 2 µM Cu |
| --- | --- | --- |
| wild-type mutant | 3.8 | 0 |
| PP303 | 14.3 | 1.4 |
| PP311 | 10.1 | 4.8 |
| PP313 | 4.5 | 2.9 |
| PP319 | 4.5 | 6.5 |
| PP323 | 3.3 | 3.9 |
| PP330 | 3.0 | 1.7 |
| PP333 | 3.3 | 5.3 |
| PP334 | 2.1 | 2.4 |
| PP336 | 19.7 | 2.7 |
| PP337 | 22.5 | 2.5 |
| PP338 | 5.8 | 7.9 |
| PP341 | 9.7 | 3.0 |
| PP342 | 22.0 | 3.0 |
| PP343 | 8.3 | 3.1 |
| PP345 | 6.9 | 2.3 |
| PP354 | 10.0 | 3.0 |
| PP358 | 13.6 | 16.4 |

[1]sMMO activity was assayed by naphthalene oxidation and expressed as µg naphthol produced per h per absorbance unit of culture density measured at 540 nm.

EXAMPLE 2

Mutants isolated in accordance with Example 1 grow well in media where methane or methanol is the sole carbon source. However, other methanotrophs occurring naturally in contaminated water samples may grow more rapidly and overgrow the mutants. In order to assure growth of only the mutants, antibiotic-resistant strains of the mutant methantrophs are readily isolated by selection from plates supplemented with antibiotics. In the following example, the spontaneous antibiotic-resistant strains are selected by directly plating on antibiotic plates. The example is illustrated with *M. trichosporium*.

Isolation of *M. trichosporium* Mutants Resistant to Antibiotics

Mutant *M. trichosporium* lacking pMMO activity were isolated according to Example 1. Thereafter, cultures were grown to late-exponential phase in Higgins MNS medium supplemented with methane and plated in 0.2 ml aliquots on Higgins MNS plates (1.8% Noble agar) supplemented with 25 mg/L rifampicin or 50 mg/L streptomycin sulfate. Plates were incubated at room temperature in desiccators with a 1:1 mixture of methane and air. After 4 weeks, colonies were transferred from the antibiotic selection plates to liquid medium containing antibiotics at the same level as the selection plates. Cultures growing at a satisfactory rate with a doubling time of less than 30 hrs were checked for constitutive sMMO phenotype by growth and expression of sMMO in medium containing copper sulfate.

PROPHETIC EXAMPLE 3

Certain methanotrophs such as *Methylosinus trichosporium* OB3b are able to utilize methanol as an alternative to methane as sole carbon and energy source. Growth of the cells on methane is not ideal for commercial applications because of the low solubility of methane in aqueous solutions, complicating bioreactor design. Additionally, the use of methane in a large-scale bioreactor presents potential explosion hazards. Although these particular disadvantages are overcome by employing methanol-grown cells, methanol adversely affects sMMO activity in *M. trichosporium* by acting as a competitive inhibitor (Davis et al., 1987; Bedard and Knowles, 1989). In addition, sMMO expression is reduced in cells grown with methanol as a sole carbon source, when compared to levels of expression found in methane-grown cultures. It is contemplated to be within the scope of this invention to overcome these problems by selecting for mutants in which sMMO inhibition by methanol is reduced, and in which expression of SMMO is improved.

In the absence of nitrate as the source of nitrogen in the growth medium, $NH_4+$ can be assimilated by methanotrophs. The first step in the assimilation of $NH_4+$ by *M. trichosporium* OB3b is the MMO-dependent oxidation to $NH_3OH$. Since sMMO performs this oxidation step more efficiently than does pMMO (Carlsen et al., 1991), the use of ammonium salts as the sole nitrogen source confers selective pressure on the cells to produce sMMO even when methanol is the carbon source. In the presence of high levels of methanol, sMMO would be saturated with methanol, making ammonium inaccessible to the cell. This selects for mutants that have acquired the ability to assimilate nitrogen, either due to an altered sMMO active site in which methanol is bound less efficiently, or to a higher level of sMMO expression which allows for sufficient ammonia oxidation in the presence of high levels of methanol. In either case, such mutants would be more effective in a bioreactor system in which cultures are grown on methanol and in which the TCE degradation cycle is continuous with the growth cycle. In addition, cultures grown with ammonium salts as sole nitrogen source and with methane as sole carbon source would have increased levels of sMMO expression, since the sMMO would be responsible for both carbon and nitrogen assimilation in surviving cells. This selection strategy may also be used to isolate mutants that overproduce sMMO.

To select for *M. trichosporium* OB3b mutants that overproduce sMMO, cells from a late-exponential culture of an sMMO-constitutive mutant, for example a streptomycin-resistant mutant of PP358, are plated on agar plates containing modified HMNS media in which nitrate salts are replaced with ammonium salts. The plates are incubated at room temperature in the presence of a 1:1 mixture of air and methane. The level of ammonium ion that competes effectively for sMMO activity against methane will be 1-100 mM, the concentration preferred is about 20 mM. Colonies that appear after 3-5 weeks of growth will be tested for the level of expression of sMMO after culturing in liquid HMNS medium. Cells are harvested from late exponential cultures by centrifugation at 8,000 ×g for 20 min at 4° C., washed in cold 25 mM MOPS, pH 7.2, and used to determine TCE activities according to Example 6. Mutants that continue to overexpress sMMO after the selection procedure are identified.

To select for *M. trichosporium* OB3b mutants that express sMMO that is highly active in the presence of methanol, cells from a late exponential phase culture of an sMMO-constitutive mutant, for example a mutant of PP358 overexpressing sMMO from the ammonium/methane selection described above, are plated on agar plates containing 0.5% methanol and modified HNMS media in which nitrate salts are replaced with ammonium salts. The level of ammonium ion that will compete effectively with methanol is a concentration between 1-100 mM, the concentration preferred is about 20 mM. Plates are incubated in a closed container to prevent methanol loss, and colonies will begin to appear after about 3-4 weeks of growth. The frequency of mutation is low, typically <10⁻⁶. The cells are then transferred into liquid HMNS media and grown with methane and with 0.5% methanol. Cultures are harvested from late exponential cultures by centrifugation at 8,000 ×g for 20 min at 4° C., washed in cold 25 mM MOPS, pH 7.2, and used to determine TCE activities according to Example 6. Mutants that exhibit elevated sMMO activity in methanol-grown cultures, relative to wild-type, are identified. The effects of methanol in mutants having the highest levels of sMMO expression will be evaluated by determining the kinetic parameters for methanol inhibition of TCE degradation. Those strains having elevated sMMO expression and a reduced level of methanol inhibition of sMMO can be used for the treatment of TCE in methanol-fed reactors, for example in the bioreactor according to Example 8, in which the growth and degradation phases are contiguous.

EXAMPLE 4

Copper tolerance in the mutants isolated as described in Example 1 was determined as illustrated in the following example by culturing in media containing up to 12 $\mu$M copper.

Growth of Cells in Presence of Copper

Figure 2A:
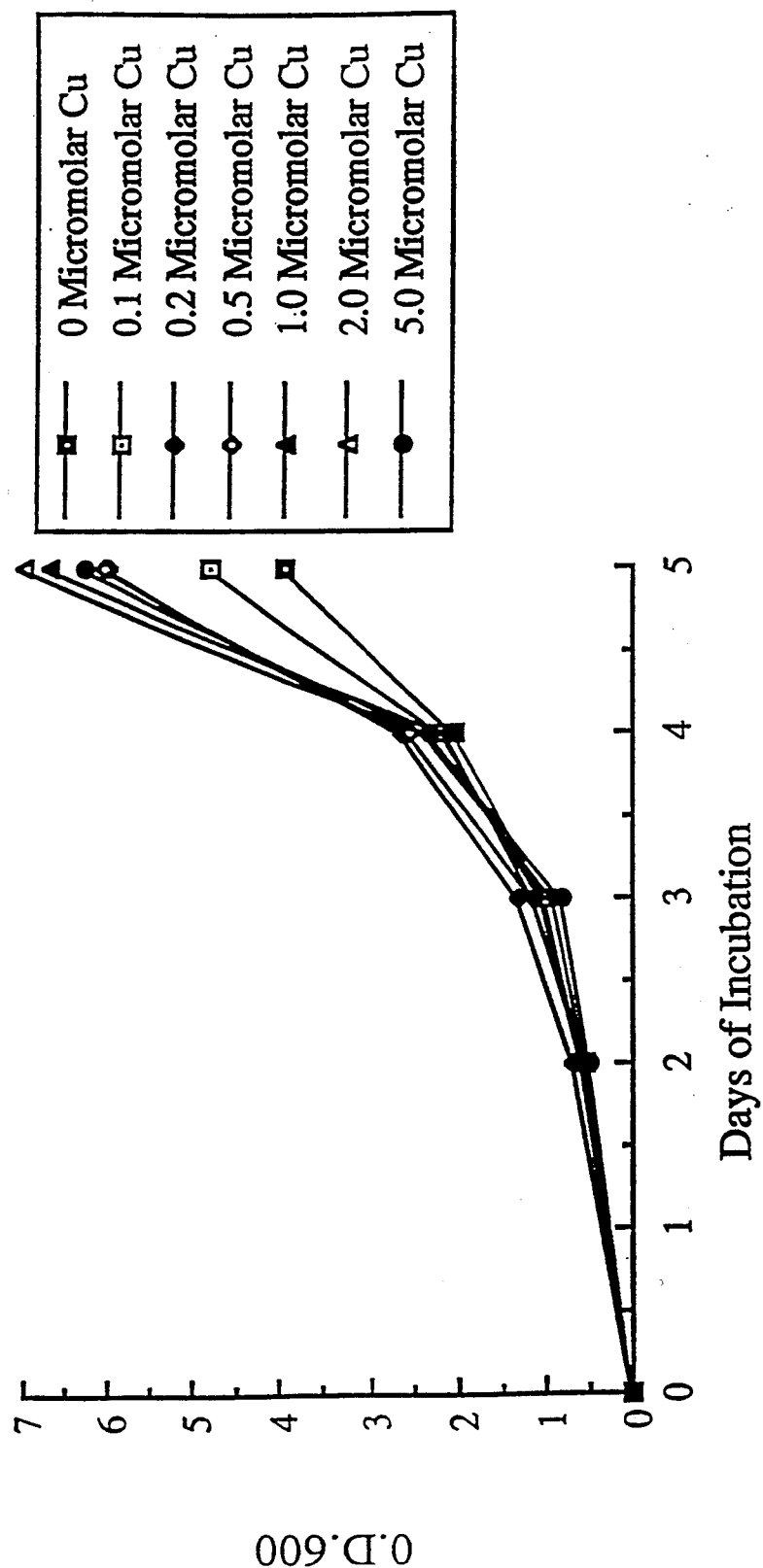
FIG. 2 shows the effects of various levels of copper sulfate on the growth of the indicated M. trichosporium OB3b mutants and wild-type. Wild-type OB3b is shown in (A); mutant PP358 in (B); mutant PP311 in (C).
Figure 2B:
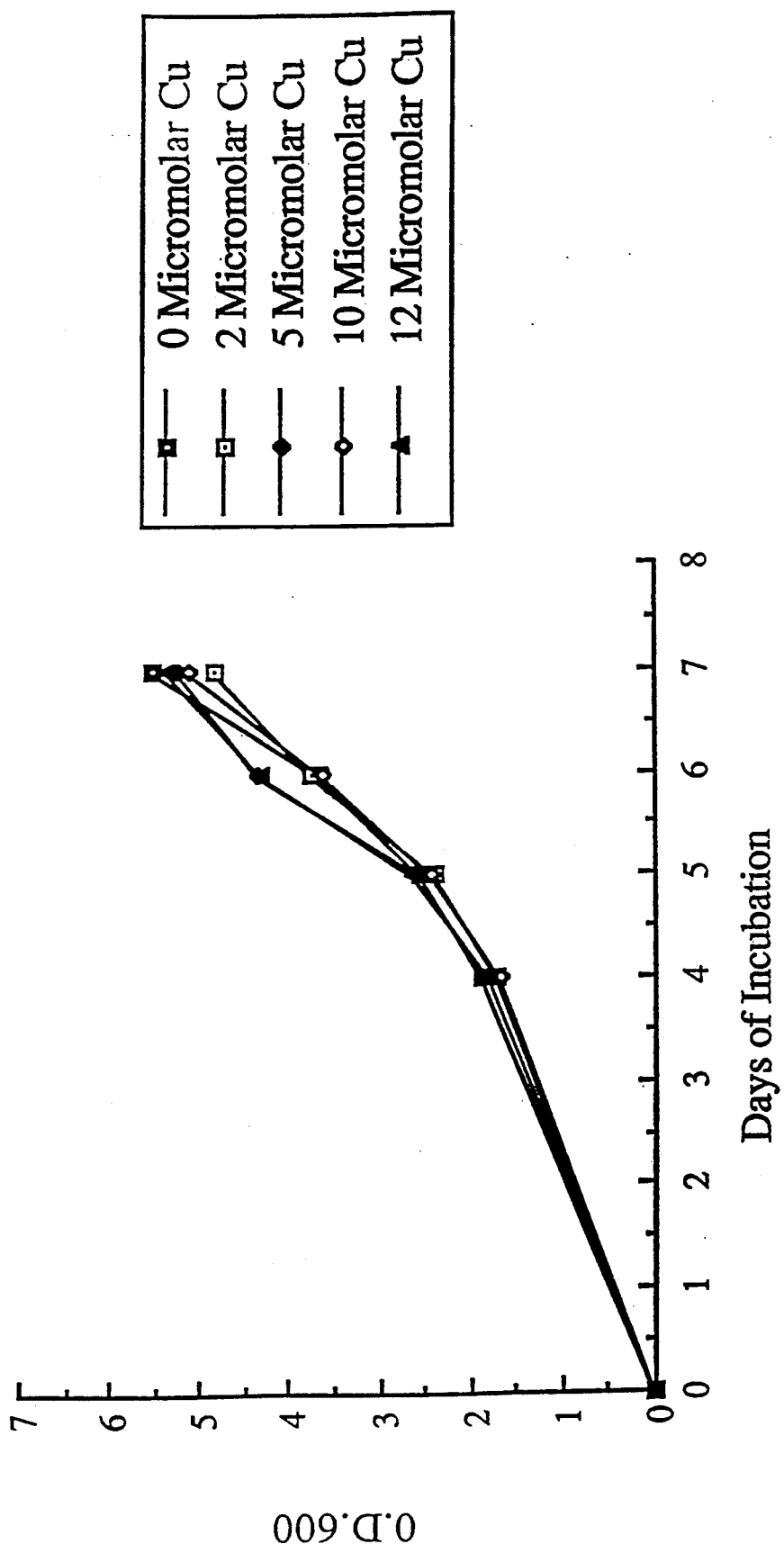
Figure 2C:
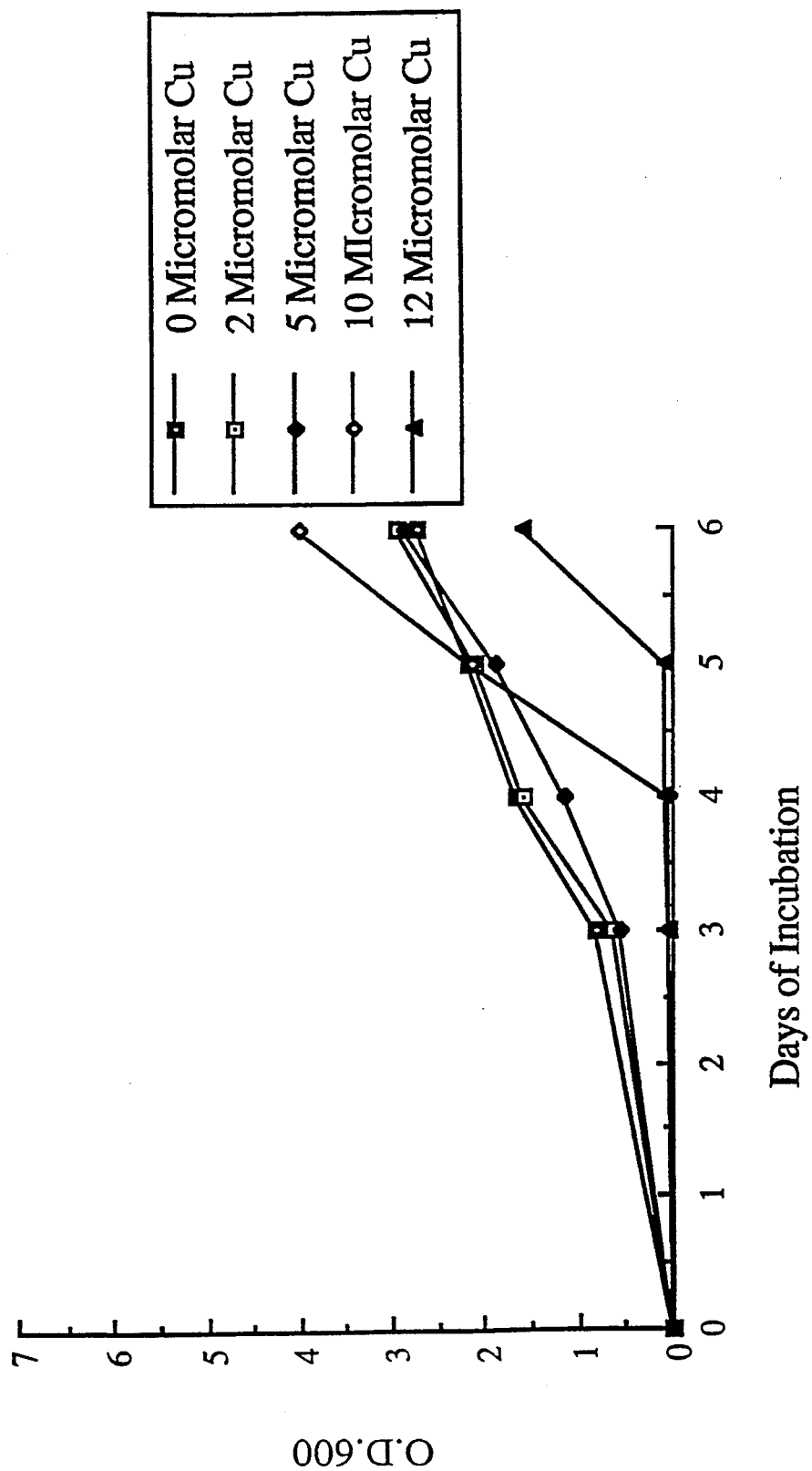

To determine the level of copper tolerance in which mutants continued to express sMMO, cultures were grown in liquid medium containing copper ranging from 2-12 $\mu$M. All mutants on initial isolation had difficulty growing in medium at this concentration of copper. Mutant PP311 and PP319 grew after a 6 day lag period in 12 $\mu$M copper, FIG. 2. When subcultured in the presence of 5 $\mu$M copper, mutants PP323, 333, and 358 became more tolerant and grew easily in 12 $\mu$M copper; however, mutants PP311 and pp319 failed to adapt to growth in 12 $\mu$M copper. FIG. 2 indicates the effect of the various levels of copper sulfate on growth of wild-type and the copper resistant mutants.

TCE degradation by whole cells was used to assay levels of sMMO. TCE disappearance was monitored as a direct measurement of sMMO levels. Cells were adjusted to a density of 0.06-0.12 absorbance units at 600 nm in 25 mM MOPS, 2 mM formate, pH 7.2, in a final volume of 16 mls in a 40 ml vial. The vial was sealed with a teflon-coated septum and 0.1 mg TCE was added. TCE levels were measured by gas chromatographic (GC) analysis of the headspace on a 30 m ×0.53 mm fused silica capillary column with a DB-624 stationary phase having a film thickness of 0.003 mm (J&W Scientific). The column was operated at 70° C., using a flame ionization detector. Activity was quantified by calculating a pseudo first-order rate constant (L/mg TSS/day). The concentration of TCE in the liquid phase was estimated at 1 mg/ml TCE from the gaseous concentration using Henry's law constant (0.4).

The five more stable mutants expressing sMMO constitutively with respect to copper concentrations had approximately the same specific activity of sMMO, as assayed by TCE decay, whether grown in the absence or presence of 5 $\mu$M copper. Generally these levels were higher than found in wild-type cells grown without copper (Table 3). The two less copper tolerant mutants, PP311 and PP319, had a lower specific activity of sMMO at levels of copper exceeding 10 $\mu$M (FIG. 1). The wild-type cultures failed to express sMMO at much lower concentrations of copper. Generally, sMMO activity was not detected in cells grown at levels above 0.5 $\mu$M Cu in batch culture, depending on the density of the culture, see FIG. 1.

TABLE 3

| | sMMO activity (L/mg TSS/day)[1] | |
|---|---|---|
| mutant | grown without Cu | grown in 5 $\mu$M Cu |
| wild-type | 0.80 (± 0.33) | 0.03 (± 0.06) |
| PP311 | 1.02 (± 0.14) | 1.15 (± 0.33) |
| PP319 | 1.06 (± 0.16) | 1.06 (± 0.40) |
| PP323 | 1.00 (± 0.39) | 1.31 (± 0.48) |
| PP333 | 1.00 (± 0.33) | 1.33 (± 0.40) |
| PP358 | 1.48 (± 0.12) | 1.45 (± 0.32) |

Levels of sMMO expression in whole cells of mutants grown in medium containing 5 $\mu$M copper.

[1]First-order rate constant for TCE disappearance from a solution initially containing 1 mg/ml TCE. Error is reported as one standard deviation from the average of at least 3 cultures.

EXAMPLE 5

Confirmation of the lack of pMMO in the methanotrophic mutants was determined as shown in the following example.

Subcellular Localization of MMO Activity

Cultures were harvested at late-exponential phase by centrifugation at 8,000 ×g for 20 min 4° C. and washed in cold 25 mM MOPS, pH 7.2. The pellet was frozen and stored at −70° C. Cells were thawed, resuspended in lysis buffer, 5 mM PIPES, pH 7.0, 5 mM $MgCl_2$ and disintegrated by two passages in a French press at 2000 psi. Debris was removed by centrifugation at 5000 ×g for 20 min at 4° C. The crude lysate was separated into soluble and particulate fractions by centrifugation at 115,000 × g for 50 min at 4° C. The membrane pellet was washed in cold lysis buffer, centrifuged again, and resuspended in lysis buffer. MMO activity was determined in the soluble and particulate fractions by propene oxidation.

In Vitro MMO Assay by Propene Oxidation

For subcellular localization of MMO activity, the enzyme was assayed by oxidation of propene. The enzyme was prepared in 25 mM PIPES, pH 7.0, at 5–7 mg/ml (soluble fraction) or 2–3 mg/ml (particulate fraction). A 1 ml aliquot of enzyme was assayed in a 9 ml vial with a teflon-coated silicone rubber septum and a 50% (v/v) mixture of propene in air. The reaction was started with addition of NADH to a final concentration of 5 mM. Propene oxide was assayed by GC analysis of the liquid phase at 47° C. Results are shown in Table 4.

TABLE 4

Subcellular localization of MMO activity, measured by propene oxidation of soluble and particulate fractions.

| mutant | % of total MMO activity in particulate fraction | |
|---|---|---|
| | cultured without Cu | cultured in 5 µM Cu |
| wild-type | 8 | 90 |
| PP311 | <0.1 | 0.15 |
| PP319 | 0.11 | 2.1 |
| PP319R | 0.70 | 100 |
| PP323 | 0 | 0 |
| PP333 | 2.0 | 0 |
| PP358 | 0 | 0 |

When cultured in 5 µM Cu, wild-type OB3b cultures expressed MMO almost entirely in the particulate fraction, while copper deficient cultures expressed MMO almost entirely in the soluble fraction, Table 2. In contrast, none of the mutants expressed MMO in the particulate fraction, even when grown in 5 µM copper sulfate. A revertant of PP319 (PP319R) lost the ability to express sMMO when grown in the presence of copper and at the same time acquired the same pattern of MMO distribution as wild-type cultures.

EXAMPLE 6

The following example illustrates the use of a rapid screen assay developed to detect sMMO activity. The method is based on the ability of sMMO to oxidize naphthalene to naphthol. Previous problems related to naphthol instability have been overcome by modification of reaction conditions. The assay works well to determine sMMO activity in liquid and in plate cultures, as shown.

Naphthalene Assay on Liquid Cultures

A 1% naphthalene solution was prepared in a 20% solution of Pluronic L-62 surfactant (BASF Corp.). The reaction was initiated by addition of the naphthalene stock to a cell suspension at 24° C. having a density of 40–100 mg TSS/L at a ratio of 1:100. The reaction was terminated after 30 min of incubation at room temperature by centrifugation at 8800 ×g for 5 min. Naphthol concentration in the supernatant was determined by a standard colorimetric procedure, using Fast Blue BN dye (tetrazotized o-dianisidine, Sigma Chemical Co., St. Louis, Mo.). In this case, 0.1 ml of a fresh 1% solution of Fast Blue BN was added. Color formation was stabilized after 15 s by addition of 0.4 ml glacial acetic acid, and naphthol was quantitated by comparing to absorbance of a standard curve at 540 nm.

In Situ sMMO Activity in Colonies by Naphthalene Oxidation Assay

Expression of sMMO in colonies growing on plates was detected by a naphthalene agar overlay assay. A stock 1% naphthalene solution in 20% Pluronic L-62 surfactant was diluted 1:25 in a 1% solution of low melting point agarose (electrophoresis grade, Bethesda Research Laboratories, Bethesda, Md.) in 25 mM MOPS, pH 7.2. After cooling to 35° C., colonies growing on agar plates were covered by 7 mls of the naphthalene top agar. After the top agar was solidified, plates were incubated at room temperature for one hour in a chamber containing 50% oxygen. Naphthol formation was detected by covering plates with 1 ml of a fresh solution of 1% Fast Blue BN. Color formed after 15 min at room temperature was stabilized by addition of 1.0 ml of glacial acetic acid. Colonies expressing sMMO developed a dark red color.

EXAMPLE 7

Differences in patterns of protein expression were exhibited by two classes of sMMO-constitutive mutants. In the less stable class, PP311 and PP319 appeared to have altered sMMO enzyme, deficient in the gamma subunit of the sMMO hydroxylase subunit. Particulate fractions from these mutants cultured in the presence of copper had an unusual pattern of protein components not found in the wild-type. On the other hand, mutants PP323, PP333 and PP358 lost copper inducibililty in the pattern of protein expression in both soluble and particulate fractions. The patterns of proteins in the particulate and soluble fractions of these mutants appeared the same as in the wild-type in the absence of copper. The following example illustrates differences in patterns of protein expression in two classes of sMMO mutants.

Classification of Mutants by SDS-PAGE

SDS-PAGE was prepared as described by Laemmli et al. (1970). This is a discontinuous system, with a 3% acrylamide/Tris buffer, pH 6.8 stacking gel over a 12% acrylamide/Tris buffer, pH 8.3 resolving gel. Gels were run in Tris/glycine buffer at 20 mamP. Lanes were loaded with approximately 10 µg of protein, and stained with Coomassie Blue. Molecular weight prestained standards (BioRad) were: 106,000; 80,000; 50,000; 32,500; 27,500, and 18,500 daltons.

Figure 3:
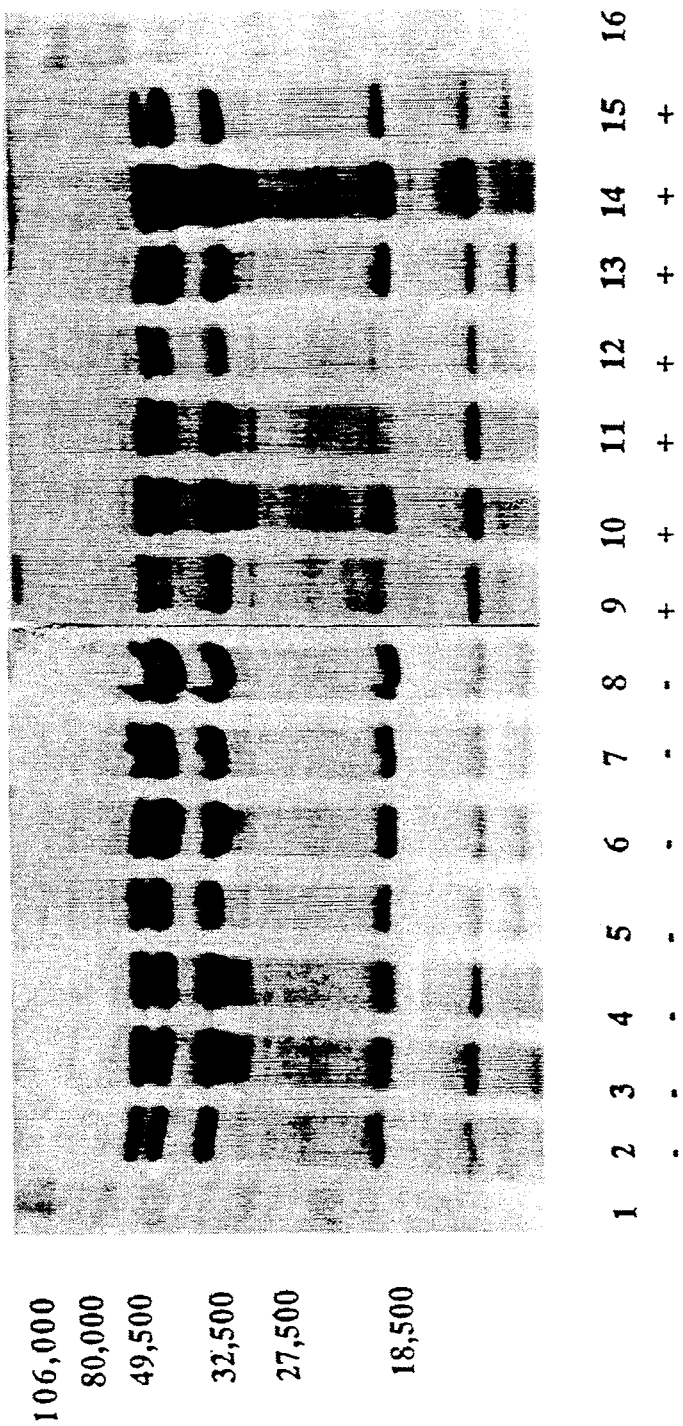
FIG. 3 shows SDS-PAGE gels of the soluble fractions of M. trichosporium OB3b mutants and wild-type. Samples are from cultures grown without copper (−) or with 5 μM copper supplementation (+). Molecular weights of standards (lanes 1 and 16) are 106,000, 80,000, 50,000, 32,500, 27,500 and 18,500. Wild-type cultures were loaded in lanes 2 and 9; PP311 in lanes 3 and 10; PP319 in lanes 4 and 11; PP319R in lanes 5 and 12; PP323 in lanes 6 and 13; PP333 in lanes 7 and 14; and PP358 in lanes 8 and 15.

The protein composition of the soluble and particulate fractions of the mutants was significantly different from that of the wild-type. The three polypeptides of the hydroxylase component of sMMO, having a molecular weight of 54,000, 45,000 and 23,000, appeared as prominent bands in SDS-PAGE of the soluble fraction of OB3b cells cultured in the absence of copper, FIG. 3A. These bands were also found in the soluble fractions of all the mutants cultured without copper. Wild-type OB3b cells cultured in the presence of 5 µM copper no longer had the prominent hydroxylase bands, but all three hydroxylase polypeptides showed prominent bands in the soluble fractions of mutants PP323, PP333 and PP358 grown in copper. These strains also exhibited an additional prominent band with an apparent molecular weight of 15,500, the approximate molecular weight of the sMMO component B. High expression of this protein was not observed in the soluble fractions of wild-type, PP311, PP319 or revertant PP319R cultures. Surprisingly, although mutants PP311, PP319 and PP319R expressed large amounts of all three of the hydroxylase components in the absence of copper, they were deficient in the prominent 23,000 molecular weight hydroxylase gamma band when cultured in 5 $\mu$M copper, FIG. 3B.

Figure 4:
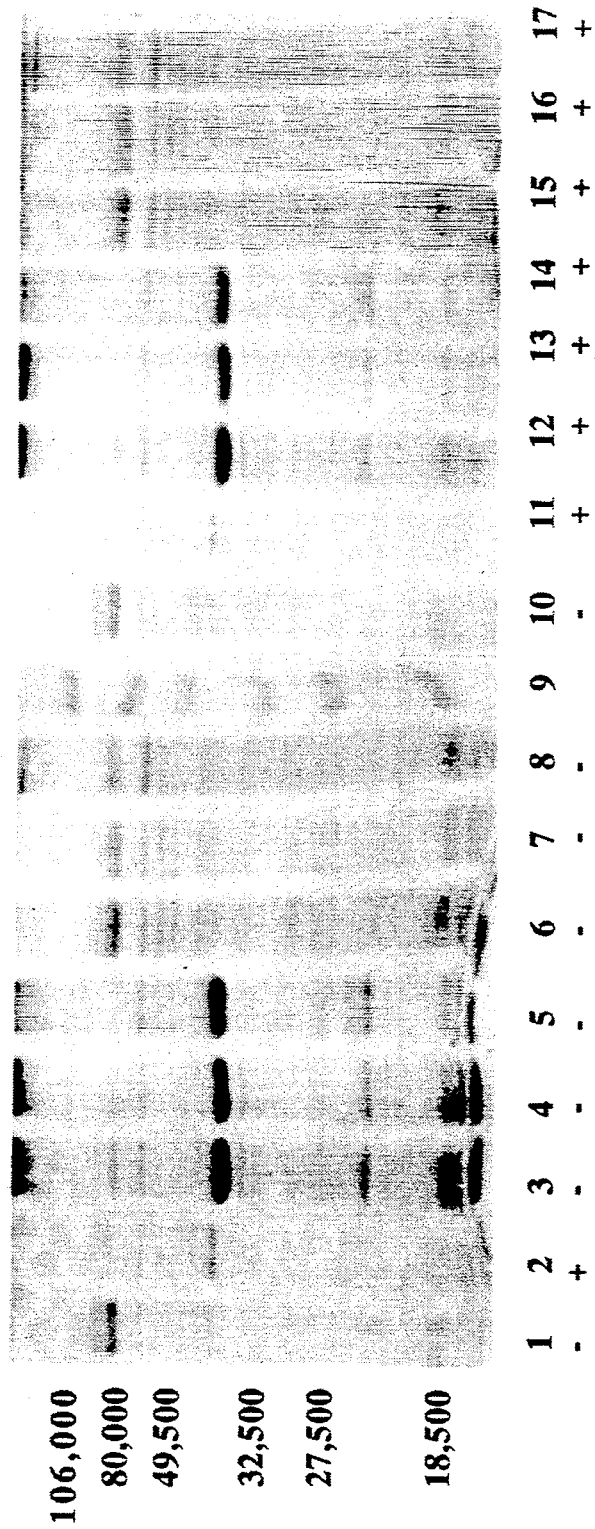
FIG. 4 shows SDS-PAGE gels of the particulate fractions of M trichosporium OB3b mutants and wild-type. Samples were from cultures lacking copper (−) or cultures grown in 5 μM copper (+). Molecular weights of standards (lane 9) are 106,000, 80,000, 50,000, 32,500, 27,500 and 18,500. Wild-type cultures were loaded in lanes 1,2,10 and 11; Pp311 in lanes 3 and 12; PP319 in lanes 4 and 13; pp319R in lanes 5 and 14; pp323 in lanes 6 and 15; pp333 in lanes 7 and 16; and pp358 in lanes 8 and 17.

In the particulate fraction, wild-type OB3b cultured in the absence of copper expressed high levels of proteins having apparent molecular weights of 80,000 and 82,000, FIG. 4A. The intensity of these protein bands was decreased in wild-type OB3b cultured in 5 $\mu$M copper, but a protein having an apparent molecular weight of 42,000 was expressed in large amounts. The proteins in the particulate fractions of mutants PP323, PP333 and PP358 were similar to those of the wild-type proteins from copper-deficient cultures, except the expression pattern in the mutants remained unchanged when grown in copper-containing medium.

The PP311 and PP319 mutants, however, expressed a dominant protein with slightly higher electrophoretic mobility than the 42 kDa protein found in copper-grown wild-type cultures. The difference in the mobility of the 42 kDa protein was reproducibly observed in different cultures of PP311, PP319 and PP319R. The protein may be a modified form of the 42 kDa protein found in the particulate fraction of wild-type cells cultured with copper, or a different protein highly expressed only in the mutants. In addition, PP311 and PP319 expressed high levels of a protein with an apparent weight of 24 kDa that was not found in the particulate fractions of wild-type or the mutant cultures. Both the 42 kDa and 24 kDa proteins in the particulate fractions of pp311, pp319 and PP319R mutant cultures differed from the wild-type proteins in the expression pattern: they were not copper inducible and were found in particulate fractions of PP311, PP319 and PP319R cultures regardless of the presence of copper in the growth medium.

EXAMPLE 8

This example illustrates a reactor useful for chlorinated solvent degradation. A novel, sequencing, packed-bed reactor is demonstrated here for treatment of TCE contaminated water. The reactor is cycled between growth and degradation modes of operation. In the growth mode, the reactor is operated in an unsubmerged condition, and methane and oxygen are supplied to the organisms from the gas phase. In the degradation mode, the reactor operates in a submerged condition and water containing the chlorinated contaminant is fed to the reactor. With this approach, a large biomass may be established in the reactor, and no enzyme competition with methane will occur during contaminant degradation. Performance of the reactor may be characterized by measurement of contaminant removal and estimation of a pseudo first order degradation rate constant through analysis of the removal data with a biofilm model (Pittmann and McCarty, 1981).

Degradation of TCE With *M. trichosporium* Mutants

The reactor was a glass column 2 inches in diameter and 3 feet long. The ends of the column were fitted with Teflon plugs and valves. The column was packed to a depth of 90 cm with diatomaceous earth pellets (Manville Celite Biocatalyst Carrier R-635), which provided physical support for the biofilm. Celite pellets were made from compressed diatomaceous earth and an inert silicate material. Pellets were cylindrical with a 0.5 cm diameter and 0.8 cm length.

Figure 5:
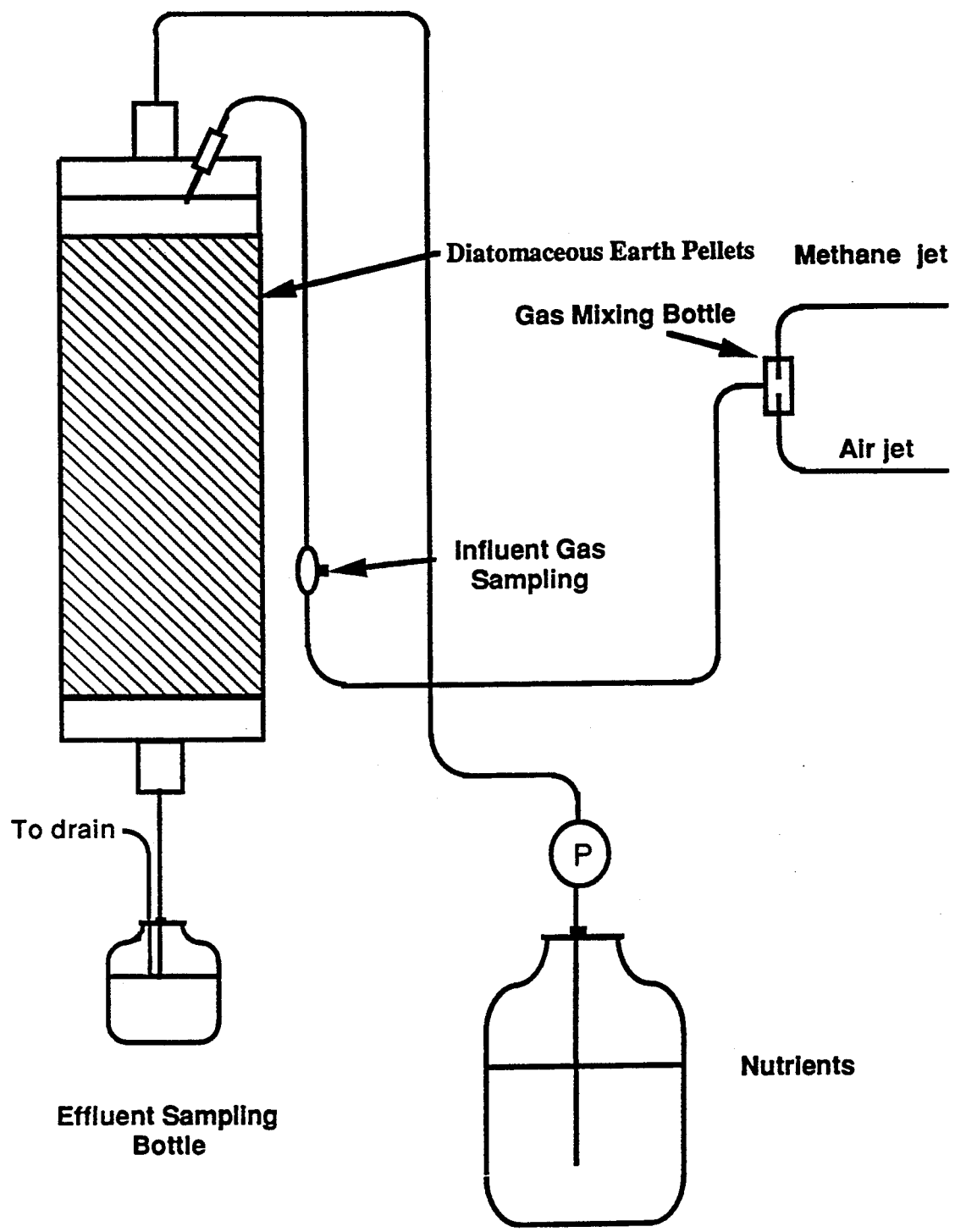
FIG. 5 is a schematic showing a bioreactor configuration employing immobilized methanotrophic bacteria for chlorinated contaminant degradation. Shown is the operation during the growth phase of operation.

During the growth mode, air and methane were supplied to the reactor at a total flow rate of 125 ml/min total. The influent methane concentration was varied from 60 to 140 mg/L of gas. A HMNS nutrient solution was trickled through the reactor at a flow rate of 2 ml/min. A 60 ml flow-through bottle was connected to the outlet of the column for gas and liquid sampling. Influent gas samples were taken from a 125 ml flow-through gas sampling bulb. A schematic of the reactor configuration during the growth mode is shown in FIG. 5.

Figure 6:
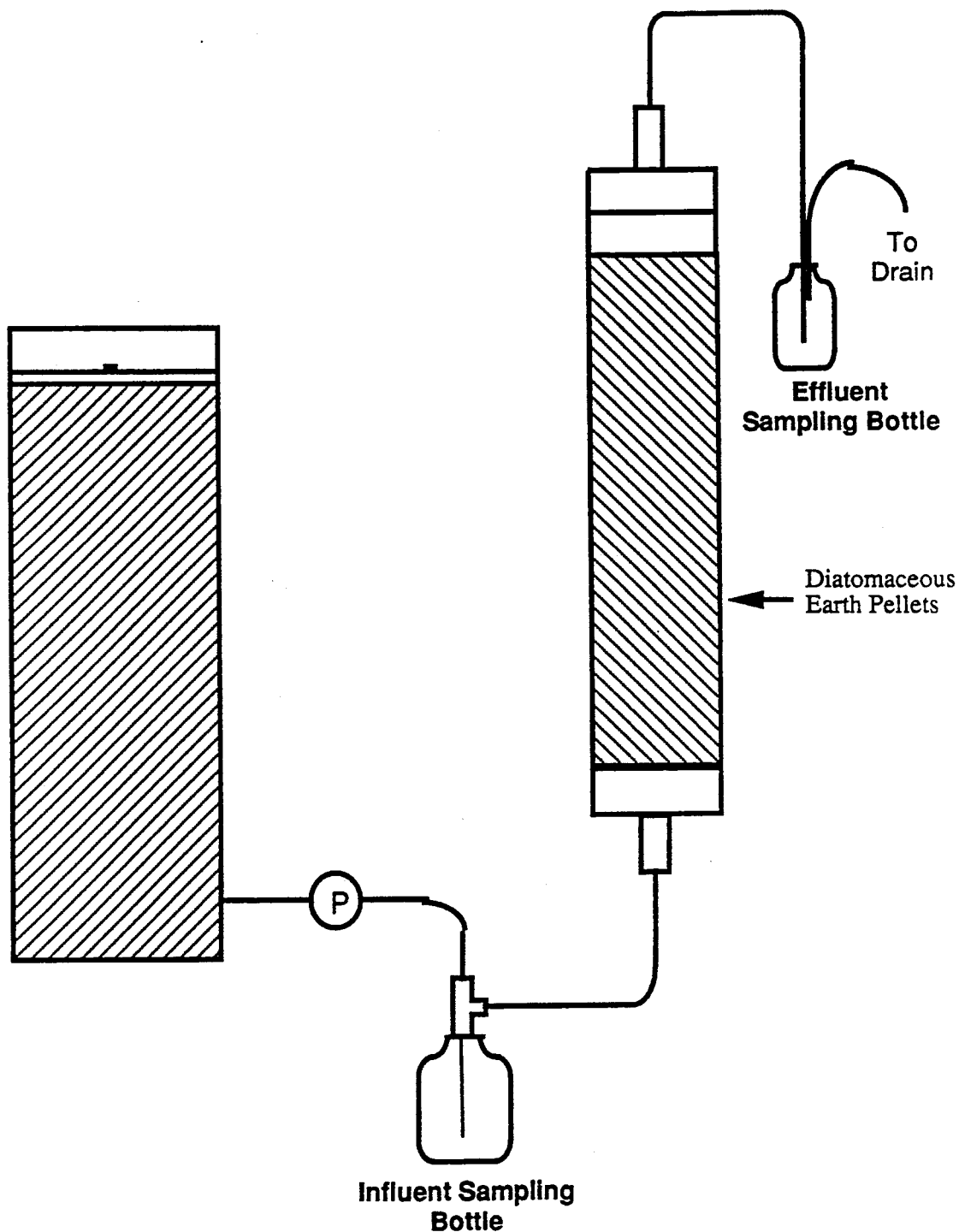
FIG. 6 is a schematic showing the bioreactor system of FIG. 5 operated in the degradation phase where a contaminated sample is introduced to the immobilized methanotrophic bacteria.

At the beginning of the degradation cycle, the column was reconfigured as shown in FIG. 6. All gas supply lines were removed and the port for gas supply to the column was plugged. Nutrients, TCE and formate were mixed with 50 l of ozonated distilled deionized water in a stainless steel, floating cover tank to minimize volatilization losses. The solution was pumped up through the column at 10 ml/min, resulting in an empty bed retention time of approximately 177 min. Flow-through sample bottles were attached to the influent and effluent ends of the column for collection of TCE and dissolved oxygen samples.

The pseudo first order rate constant for TCE degradation was estimated by measuring TCE removal across the column during the degradation cycle and biomass within the column. A biofilm computer model was used to indirectly estimate rate constant data. The mutant had a rate constant of 0.02 L/mg TSS/day, while wild-type had a rate constant of 0.0008 L/mg TSS/day at an influent TCE concentration of 75 $\mu$g/L. The mutant thus degraded TCE 25 times faster than the wild-type.

EXAMPLE 9

The following example illustrates immobilization of a methanotrophic mutant on diatomaceous earth pellets with retention of sMMO activity. This contrasts with immobilization of wild-type *M. trichosporium* OB3b which causes a significant decrease in sMMO activity.

Effect Immobilization on Growth and sMMO Expression

Diatomaceous earth (DE) is a highly porous rigid medium useful as a support in biofilm reactors. Its large surface area allows for attachment of a large number of cells and its rigidity allows for design of large, incompressible columns. Naturally occurring diatoms generally contain detectable levels of leachable copper. This example illustrates the effects of leached copper on sMMO activity of wild-type *M. trichosporium* compared with mutant M. trichosporium PP358.

Cultures of wild-type and mutant *M. trichosporium* were grown in sealed 40 ml vials to which 4 ml of Higgins minimal nitrate salts was added. Cultures were initiated with a 4% (v/v) inoculum from an actively growing liquid culture in the same medium. Methane and oxygen were maintained in the headspace at 25% (v/v) by daily supplementation.

Diatomaceous earth was pulverized to a fine powder in a mortar and pestle and sterilized by autoclaving in culture vials. Diatomaceous earth powder was added to the 4 ml liquid medium at the following levels: 0.1 g, 1.0 g, 2.0 g and 3.0 g.

Activity of sMMO was determined by the naphthalene oxidation assay according to Example 6 in which whole cells were incubated with naphthalene and naphthol production detected by addition of Fast Blue BN dye. The growth rate was determined by assaying for electron transport activity, developed for measurement of microbial activity in soil samples (Trevors et al., 1982). The reduction of a 0.04% solution of 2-(p-iodophenyl)-3-(p-nitrophenyl)-5-phenyl tetrazolium chloride (INT) to iodonitrotetrazolium formazan (INT-formazan) by whole cells was assayed by extraction of product into 10 volumes of methanol followed by direct measurement of absorption at 480 nm.

Figure 7:
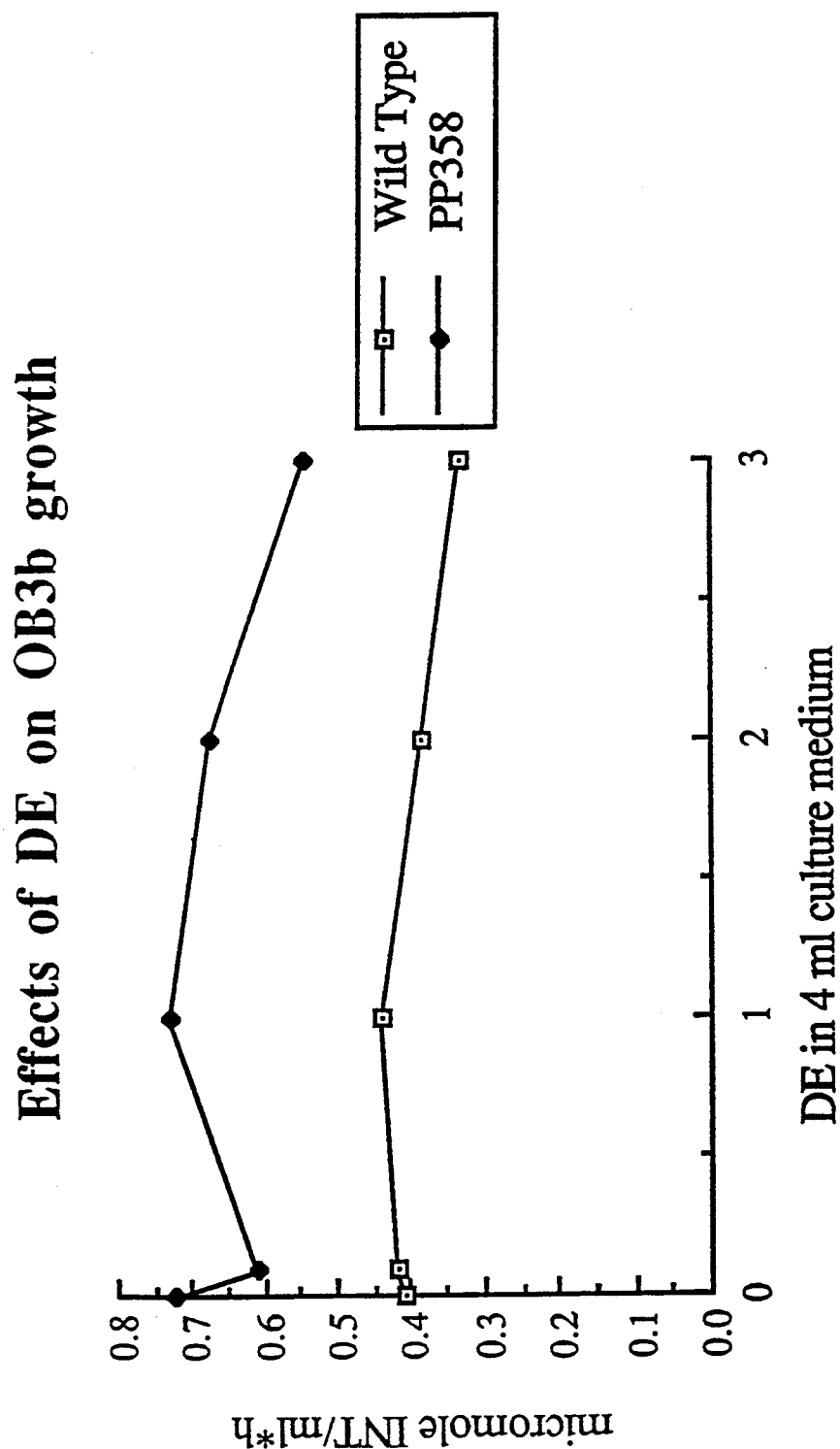
FIG. 7 shows the effects of diatomaceous earth addition on the viability of cultures of Methylosinus trichosporium OB3b wild-type (□) and copper resistant mutant PP358 (+).

FIG. 7 shows the effects of powdered diatomaceous earth on the growth rate of wild-type and copper-resistant mutant PP358. There was a slightly smaller ETS activity with increasing levels of diatomaceous earth addition, but the difference was small; activity at 3 g DE/4 ml culture medium was less than 15% lower that the level of activity in the absence of diatomaceous earth.

Figure 8:
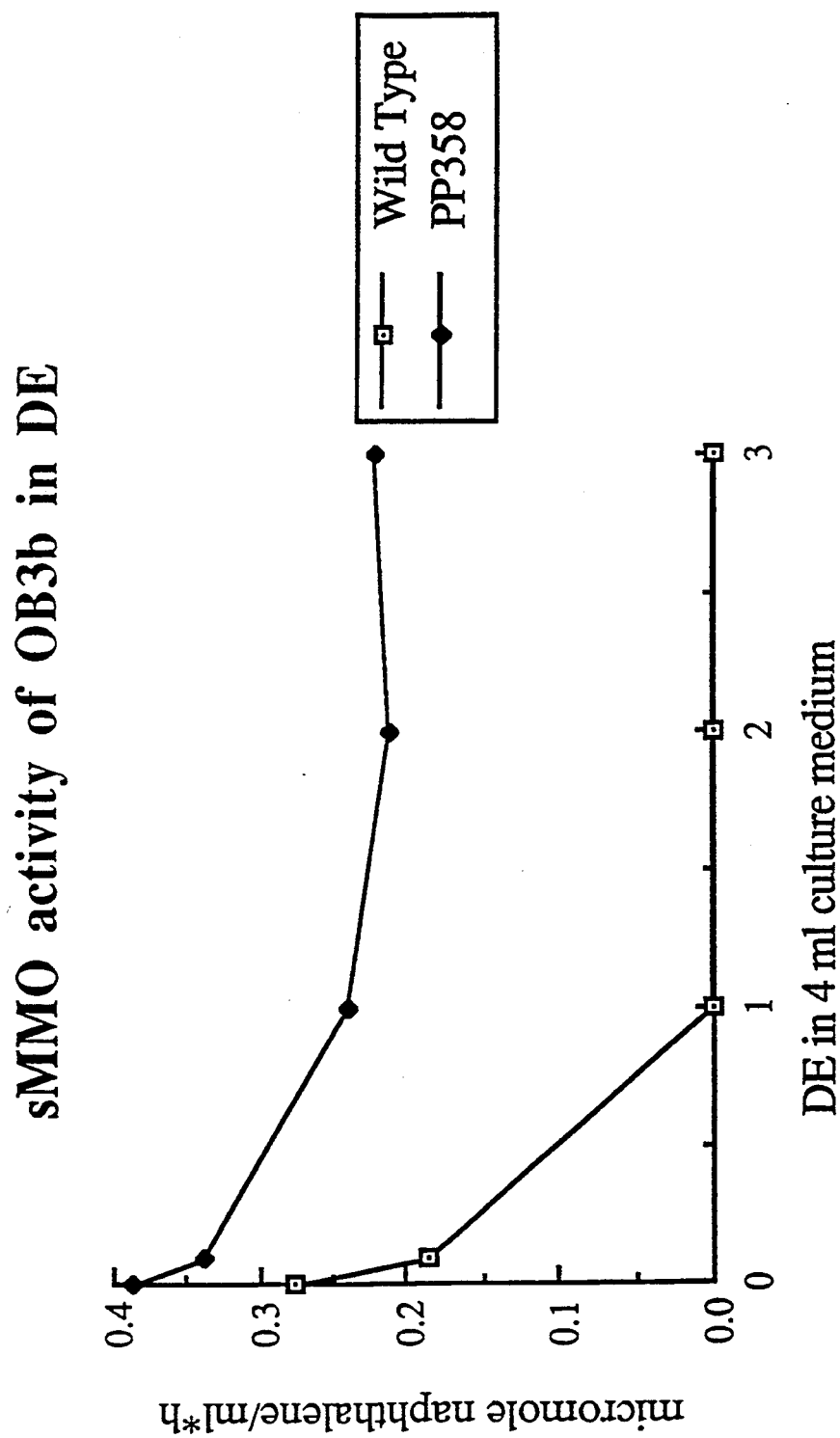
FIG. 8 shows the effects of diatomaceous earth addition on expression of sMMO in cultures of Methylosinus trichosporium OB3b wild-type (□) and copper-resistant mutant PP358 (+) determined as μmole naphthalene produced per ml per hr.

FIG. 8 shows the effects of powdered diatomaceous earth on the levels of sMMO expression in cultures of wild-type and copper-resistant mutant PP358. The wild-type OB3b was highly susceptible to diatomaceous earth: at the lowest level of addition (0.1 g DE/4 ml culture medium), activity was reduced by 33% and was essentially undetectable at all other levels of diatomaceous earth addition. In contrast, the copper-resistant mutant continued to express active sMMO at the highest levels of diatomaceous earth addition at approximately 55% of activities in cultures without diatomaceous earth.

PROPHETIC EXAMPLE 10

This example illustrates one of several contemplated methods to be employed when treating water samples contaminated with chlorinated solvents and other chemicals such as heavy metals or toxic organics. The other chemicals may adversely affect methanotropic species, including wild-type and mutants, effectively diminishing the rate of chlorinated hydrocarbon degradation. The particular method illustrated contemplates the use of hollow fiber membrane reactors.

Bioremediation of Volatile Chlorinated Hydrocarbons

The reactor consists of a shell packed with small diameter hydrophobic membranes (e.g., polypropylene). One configuration consists of 5600 hollow fibers, each with an inner diameter of 240 μm. Operation comprises passing the contaminated water through the lumen while recirculating a solution containing the bacteria through the shell side of the reactor. The volatility of the chlorinated hydrocarbon causes it to move first into the gas phase within the fiber membrane and then to the organisms on the shell side. Chemicals that inhibit the organisms, such as various metals, are unable to cross the membrane. In this way, essentially two separate environments are maintained within a single reactor. The pore size within the hollow fibers also is such that microorganisms cannot pass across the fibers. Thus, the reactor design is helpful in preventing contamination of the pur culture with other bacteria.

The contaminated water, containing 100 μg/L of TCE, is pumped through the lumen side of the reactor at a flow rate of 5 mL/min, which provides a hydraulic retention time in the reactor of about 30 minutes. The solution containing the bacteria is circulated through the shell side at a flow rate of 16 mL/min, which provides a hydraulic retention time of approximately 20 minutes per pass. The concentration of bacteria in the solution is maintained at 100 to 500 mg TSS/L. The total volume of the bacterial solution is about 4 L, which is more than 10 times the volume of the shell side of the reactor. The majority of the bacterial solution is in a separate, completely mixed reservoir and the hollow fiber membrane reactor. In one application of the technology, the organisms are first grown in a batch reactor and placed in the reservoir, where they are recirculated into the hollow fiber membrane reactor until their ability to degrade chlorinated solvents declines to an unacceptably low level. The organisms are then replaced with a new batch of bacteria. Another possibility is to supply both methane and oxygen to the reservoir, so that the organisms are continually resupplied with the growth substrate. This will lengthen the period of successful operation. A third possibility is to operate the reservoir as a continuous-flow chemostat so that organisms are continuously being grown and removed from the system. This configuration permits indefinite operation of the reactor, as opposed to the first two, which require periodic replacement of the organisms.

Reactor performance is characterized by measuring the influent and effluent TCE concentrations on the lumen side, as well as the effluent TCE concentration from the shell side. Ideally, the effluent TCE concentration on the shell side should be virtually undetectable because the organisms should degrade all the TCE that crosses the membranes.

PROPHETIC EXAMPLE 11

The following example illustrates a contemplated use of methanotrophic mutants according to Example 2 in a sequencing, packed reactor. Attachment media in the sequencing reactor is in contact with contaminated water during the degradation cycle of operation. Other microorganisms from the contaminated water may attach to the media. Other methanotrophs with markedly smaller capacity for degrading chlorinated solvents may displace the mutants due to a more rapid growth rate, causing deterioration of process performance. Displacement is a concern because the mutants are slower growing than wild-type methanotrophs and because toxicity of the chlorinated contaminant intermediates (e.g., TCE epoxide) places a metabolic burden on the mutants not experienced by the other organisms.

Streptomycin and nalidixic acid are placed in the nutrient solution trickled through the reactor during the growth mode of the operation. The presence of these chemicals should greatly diminish the ability of organisms other than the mutants to grow in the reactor. All other operating conditions are maintained substantially according to Example 8.

REFERENCES

The references listed below are incorporated herein by reference to the extent that they supplement, explain, provide a background for or teach methodology, techniques and/or compositions employed herein.

Bedard, C. and Knowles, R. (1989) "Physiology, biochemistry and specific inhibitors of $CH_4NH_4^+$ and CO oxidation by methanotrophs and nitrifiers" *Microbiol. Reviews* 53:68–84.

Bradford, M. M. (1976) "A rapid and sensitive method for the quantitation of microgram quantities of protein utilizing the principle of protein-dye binding", *Anal. Biochem.* 72:248–252.

Burrows, K. J., Cornish, A., Scott, D. and I. J. Higgins (1984) "Substrate specifications of the soluble and particular methane monooxygenases of *Methylosinus trichosporium* OB3b expressing soluble methane monooxygenase", *Appl. Env. Microbiol.*, 55:2819–2826.

Cornish, A., Nicholis, K. M., Scott, P., Hunter, B. K., Aston, W. J., Higgins, I. J., and J. K. M Sanders "In vivo $^{13}C$ NMR investigations of methanol oxidation by the obligate methanotroph *Methylosinus trichosporium* OB3b", *J. Gen. Microbiol.*, 133:291–296.

Cardy, D. L. N., Laidler, V., Salmond, G. P. C., and Murrell, J. C. (1991) "Molecular Analysis of the Methane Monooxygenase (MMO) gene cluster of *Methylosinus trichosporium* OB3b". *Molecular Microbiology* 5:335–342.

Carlsen, H. N., Joergensen, L. and Degn, H. (1991) "Inhibition by ammonia of methane utilization in *Methyloccus capsulatus* (Bath)" *Appl. Microbiol. Biotechnol.* 35:124–127.

Davis, K. I., Cornish, A. and Higgins, I. J. (1987) "Regulation of the intracellular location of methane monooxygenase during growth of *Methylosinus trichosporium* OB3b on methanol", *J. Gen. Microbiol.* 133:291–297.

De Flora, S., Zanacchi, P. Camoirano, A., Bennicelli, C. and Badolati, G. S. (1984) "Genotoxic activity and potency of 135 compounds in the Ames reversion test and in a bacterial DNA-repair test", *Mutation Res.* 133:161–198.

Fan, A. M. (1988) "Trichloroethylene: water contamination and health risk assessment," *Rev. Env. Contam. Toxicol*, 101:55–92.

Fliermans, C. B., Phelps, T. J., Ringelberg, D., Mikell, A. T., and D. C. White (1988) "Mineralization of trichloroethylene by heterotrophic enrichment cultures", *Appl. Env. Microbiol.*, 5:1709–1714.

Forstner, U., and G. T. W. Wittman (1979) *Metal Pollution in the Aquatic Environment*, Springer-Verlag. p.356.

Green, T. (1983) "The activation of dichloromethane and chlorofluoromethane in a bacterial mutation assay using *Salmonella typhimurium*", *Mutation Res.*, 118:277–288.

Hansen, R. S., Tsien, H. C., Brusseau, G. A. an L. P. Wackett (1990) "Biodegradation of low-molecular-weight halogenated hydrocarbons by methanotrophic bacteria", FEMS *Microbiol. Lett.*, 87a;2-73–278.

Infante, P. F. and T. A. Tsongas (1987) "Mutagenic and oncogenic effects of chloromethanes, chloroethanes, and halogenated analogues of vinyl chloride," *Env. Sci. Res.*, 25:301–327.

Jongen, W. M. F., Alink, G. M., and J. H. Koeman (1978) "Mutagenic effect of dichloromethane on Salmonella typhimurium", *Mutation Res.*, 56:245–248.

Laemmli, U. K. 1970. "Cleavage of Structural Proteins During the Assembly of the Head of the Bacgeriophage T4"*Nature* (London) 277: 680–685.

McPheat, W. L., Mann, N. H., and H. Dalton (1987) "Isolation of mutants of the obligate methanotroph *Methylomonas albus* defective in growth on methane", *Arch. Microbiol,* 148:40–43.

Nicolaidis, A. A., and A. W. Sargent (1987) "Isolation of methane monooxygenase-deficient mutants from *Methylosinus trichosporium* OB3b using dichloromethane", *FEMS Microbiol. Lett.,* 41:47–52.

Oldenhuis, R., Vink, R. L. J. M., Hansen, D. B. and B. Wiltholt (1989) "Degradation of chlorinated aliphatic hydrocarbons by *Methylosinus trichosporium* OB3b expressing soluble methane monooxygenase", *Appl. Envir. Microbiol.,* 55:2819–2826.

Parsons, F., Wood, P. R. and DeMarco (1984) "Transformations of tetrachloroethylene and trichloroethylene in microcosms and groundwater", *J. Am. Water Works Assoc.,* 76:56–59.

Patel, R. N., Hou, C. T., Laskin, A. I., and A. Felix (1982) "Microbial oxidation of hydrocarbons: properties of a soluble methane monooxygenase from a facultative methane-utilizing organism, *Methylobacterium* sp. strain CRL-26", *Appl. Envir. Microbiol.,* 44:1130–1137.

Pittmann, B. E. and McCarty. P. L. (1981) "Substrate flux into biofilms of any thickness", *J. Environ. Engrg. ASCE* 107: 831–849.

Snell, F. D., and C. T. Snell (1971) *Colorimetric Methods of Analysis.* Van Nostrand Reinhold Co., pp.55–56.

Stanley, S. H., Prior, S. D., Leak, D. J. and H. Dalton (1983) "Copper stress underlies the fundamental change in intracellular location of methane monooxygenase in methane-oxidizing organisms: studies in batch and continuous cultures", *Biotechnol. Lett.,* 5:487–492.

Trevors, J. T., Mayfield, C. I., and Inniss, W. E. (1982) "Measurement of Electron Transport System (ETS) Activity in Soil," *Microbial Ecology* 8, 163–168.

Tsien, H. -C. and R. S. Hanson, (1992) "soluble methane monooxygenase component B gene probe for identification of methanotrophs that rapidly degrade trichloroethylene", *Appl Env. Microbiol.* 58:953–960.

Wilson, J. T., and B. H. Wilson (1985) "Biotransformation of trichloroethylene in soil," *App. Env. Microbiol.* 49:242–243.

What is claimed is:

1. A mutant methanotrophic bacterium having constitutive sMMO activity in the presence of copper ion concentrations between about 1 $\mu M$ copper ion and about 18 $\mu M$ copper ion, wherein the mutant methanotrophic bacterium is selected from a group consisting of *Methylosinus trichosporium*, *Methylococcus capsulatus*, *Methylosinus methanica* 81Z, *Methylosinus sporium*, *Methylosinus sp.* B and *Methylobacterium sp.* strain CRL26.

2. The mutant methanotrophic bacterium of claim 1 which has antibiotic resistance to rifampicin B or streptomycin.

3. A mutant methanotrophic bacterium which is identified as *Methylosinus trichosporium* ATCC 55314.

4. The mutant of claim 1 or claim 2 wherein the copper ion concentration is from about 1 to about 15 $\mu M$.

5. The mutant of claim 1 or claim 2 wherein the copper ion concentration is about 12 $\mu M$.

* * * * *